United States Patent [19]

Takehara et al.

[11] Patent Number: 5,061,398
[45] Date of Patent: Oct. 29, 1991

[54] OPTICALLY ACTIVE LACTONE DERIVATIVE, INTERMEDIATE THEREFOR, PROCESS FOR PRODUCING THE INTERMEDIATE, LIQUID-CRYSTAL COMPOSITION, AND LIQUID-CRYSTAL DISPLAY DEVICE

[75] Inventors: Sadao Takehara; Takeshi Kuriyama; Kayoko Nakamura; Tadao Shoji, all of Chiba; Toru Fujisawa, Saitama; Masashi Osawa, Chiba; Tamejiro Hiyama; Tetsuo Kusumoto, both of Kanagawa; Akiko Nakayama, Tokyo; Kiyoharu Nishide, Shiga, all of Japan

[73] Assignees: Dainippon Ink and Chemicals, Inc., Tokyo; Kawamura Institute of Chemical Research, Sakura; Sagami Chemical Research Center, Tokyo, all of Japan

[21] Appl. No.: 515,915

[22] Filed: Apr. 27, 1990

[30] Foreign Application Priority Data

Apr. 28, 1989 [JP] Japan ................... 1-107850

[51] Int. Cl.$^5$ ............ C09K 19/34; C09K 19/30; C09K 19/52; C07D 307/93
[52] U.S. Cl. ................. 252/299.61; 252/299.01; 549/458
[58] Field of Search ............. 252/296.01, 299.02, 252/299.6, 299.62, 299.63, 299.64, 299.65, 299.66, 299.67; 350/350 S, 350 R; 549/263, 295, 296, 297, 299, 322, 392, 456, 458, 475

[56] References Cited

U.S. PATENT DOCUMENTS

| | | | |
|---|---|---|---|
| 4,818,431 | 4/1989 | Eidenschink et al. | 252/299.61 |
| 4,909,957 | 3/1990 | Sakaguchi et al. | 252/299.61 |
| 4,973,425 | 11/1990 | Kazuhiko et al. | 252/299.61 |

FOREIGN PATENT DOCUMENTS

| | | |
|---|---|---|
| 0117476 | 2/1984 | European Pat. Off. |
| 0306919 | 9/1988 | European Pat. Off. |
| 3017499 | 11/1980 | Fed. Rep. of Germany |

*Primary Examiner*—John S. Maples
*Assistant Examiner*—Shean C. Wu
*Attorney, Agent, or Firm*—Armstrong, Nikaido, Marmelstein, Kubovcik & Murray

[57] ABSTRACT

An optically active lactone derivative represented by the following general formula (I):

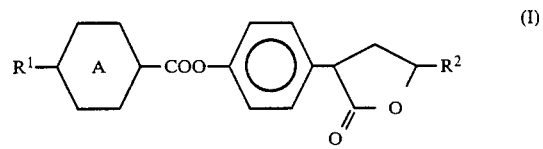

wherein $R^1$ represents a straight-chain or branched alkyl, alkoxyl, alkanoyloxy, alkoxycarbonyl, alkoxyalkyl, alkoxyalkanoyloxy, or alkoxyalkoxyl group having 1 to 20 carbon atoms or an optically active group of each of the above kinds, $R^2$ represents a straight-chain or branched alkyl group having 1 to 20 carbon atoms,

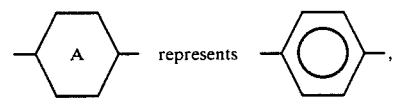

represents

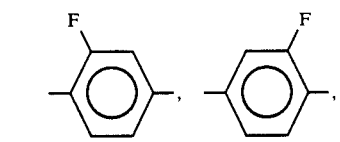

or trans-1,4-cyclohexylene group of the formula

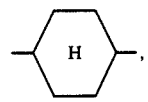

and the asymmetric carbon atoms at the 2- and 4-positions in the lactone ring each independently is of the (S) or (R) configuration, an intermediate therefor, a process for producing the intermediate, a liquid-crystal composition, and a liquid-crystal display device.

28 Claims, No Drawings

OPTICALLY ACTIVE LACTONE DERIVATIVE, INTERMEDIATE THEREFOR, PROCESS FOR PRODUCING THE INTERMEDIATE, LIQUID-CRYSTAL COMPOSITION, AND LIQUID-CRYSTAL DISPLAY DEVICE

FIELD OF THE INVENTION

The present invention relates to a novel optically active compound, a process for producing the same, a liquid-crystal composition, and a liquid-crystal display device. More particularly, it relates to a ferroelectric liquid-crystal display material having excellent response characteristics and a raw material therefor.

BACKGROUND OF THE INVENTION

Liquid-crystal display devices are now used extensively owing to their excellent characteristics (low-voltage operation; small power consumption; thin displays can be constructed; displays can be used in bright light and do not cause the viewer to suffer eyestrain). However, the most commonly used TN type display system is very slow in response compared to light-emitting display systems such as the CRT type and, further, it cannot memorize the information being displayed after the applied electric field is removed (it has no memory effect). Because of these disadvantages, many limitations have been imposed on the application of the TN type displays to a light shutter that is required to have high-speed response characteristics, a printer head, dynamic pictures that should be driven time-division-wise, such as those in TVs, etc. Therefore, the TN type displays are unsuited for these applications.

Recently, a display system employing a ferroelectric liquid crystal was reported by Mayer et al. Since both high-speed response as high as 100 to 1,000 times that of the TN type and memory effect can be obtained with the proposed display system, ferroelectric liquid crystals are expected to be a next-generation liquid-crystal display device and studies and developments are currently being made extensively.

The liquid crystal phases of ferroelectric liquid crystals belong to the chiral smectic phases of the tilt type, but from the practical standpoint, those exhibiting a chiral smectic C (hereinafter abbreviated as Sc*) phase, which is the lowest in viscosity among the chiral smectic phases, are most preferable.

A large number of liquid-crystal compounds that exhibit an Sc* phase have been synthesized and studied. For use as a ferroelectric display device, such liquid-crystal materials are preferably required: (A) that exhibit an Sc* phase over a wide temperature range including room temperature; (B) that have a proper phase sequence on the high-temperature side of the Sc* phase, with the helical pitch thereof being large, in order to obtain good orientation; (C) that have proper tilt angles; (D) that have low viscosities; and (E) that show spontaneous polarization that is strong to some degree. However, there is no known liquid-crystal compound which alone satisfies all of these.

Therefore, liquid-crystal compositions that exhibit an Sc* phase (hereinafter referred to as Sc* liquid-crystal compositions) are being used. An Sc* liquid-crystal composition is prepared by a method in which liquid-crystal compounds that mainly exhibit an Sc* phase (hereinafter referred to as Sc* liquid-crystal compounds) are mixed, or by a method in which an optically active compound or composition is added as a chiral dopant to an optically inactive liquid-crystal composition that exhibits an Sc phase (hereinafter referred to as an Sc liquid-crystal composition). However, since Sc liquid-crystal compositions have lower viscosities than Sc* liquid-crystal compositions, the latter method is suited for high-speed response and is commonly employed. Although a chiral dopant is not necessarily required to exhibit an Sc* phase as well as a liquid-crystal nature, the preferred chiral dopant is the one which, when incorporated in an Sc liquid-crystal composition, does not lower the transition temperatures of the composition to a large extent and which can induce a sufficiently strong spontaneous polarization by incorporation thereof in an amount as small as possible, from the standpoint of enabling the resulting Sc* liquid-crystal composition to have a low viscosity so as to attain high-speed response. Known optically active compounds are insufficient to constitute such a chiral dopant and, hence, there has been a need for a compound which shows stronger spontaneous polarization.

It is already known that in order that a compound can show strong spontaneous polarization, it is preferable that an asymmetric center and a dipole in the compound molecule be positioned as close together as possible and also as close to the liquid-crystal core as possible and the dipole be as strong as possible. It is further desirable that the dipole be inhibited to some degree from freely rotating on the long axis of the liquid-crystal molecule.

From the above, it is thought that a compound in which a strong dipole such as a carbonyl group, cyano group, etc. has been fixed on a ring structure and this ring structure contains an asymmetric center therein is desirable in order to obtain strong spontaneous polarization. As such a compound, however, only a compound containing a slightly optically active epoxide is known (Abstracts of the 14th Symposium on Liquid Crystals, 1988, Sendai, Japan, p. 20), and there has so far been no known compound containing in its ring structure a carbonyl group which is a stronger dipole.

SUMMARY OF THE INVENTION

As described above, the conventional compounds, when used as chiral dopants, can only induce insufficient spontaneous polarization. Hence, there has been a desire for improvement of such conventional compounds so as to obtain an Sc* liquid-crystal composition with good high-speed response.

Accordingly, an object of the present invention is to provide a novel, optically active compound which can induce sufficiently strong spontaneous polarization when used as a constituent of a chiral dopant even in a small amount.

Other objects of the present invention are to provide an intermediate for the above compound, a process for synthesizing the intermediate, and a ferroelectric liquid-crystal composition which employs the above compound and has high-speed response characteristics and further to provide a liquid-crystal display device.

DETAILED DESCRIPTION OF THE INVENTION

According to one aspect of the present invention, there is provided an optically active lactone derivative represented by the following general formula (I):

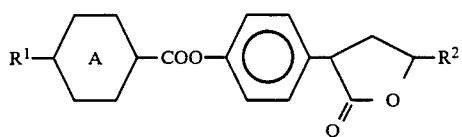
(I)

wherein R¹ represents a straight-chain or branched alkyl, alkoxyl, alkanoyloxy, alkoxycarbonyl, alkoxyalkyl, alkoxyalkanoyloxy, or alkoxyalkoxyl group having 1 to 20 carbon atoms or an optically active group of each of the above kinds, R² represents a straight-chain or branched alkyl group having 1 to 20 carbon atoms,

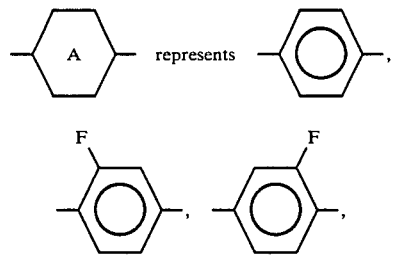

or trans-1, 4-cyclohexylene group of the formula

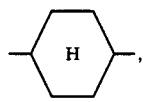

and the asymmetric carbon atoms at the 2- and 4-positions in the lactone ring each independently is of the (S) or (R) configuration.

According to other aspects of the present invention, there are provided an intermediate for the compound of general formula (I) given above, a process for producing the intermediate, a liquid-crystal composition comprising the compound of general formula (I), and a liquid-crystal display element employing the liquid-crystal composition.

The present invention is explained below in detail.

In general formula (I) above, in the case where

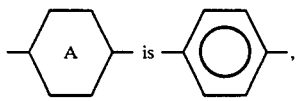

R¹ is preferably a straight-chain branched alkyl or alkoxyl group having 1 to 20 carbon atoms or an optically active group of each of the above kinds. In the case where

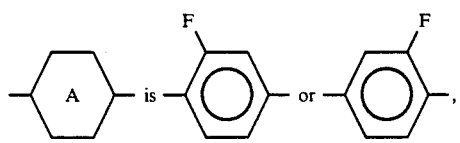

R¹ is preferably a straight-chain or branched alkoxyl group having 1 to 20 carbon atoms or an optically active group of the above kind. In the case where

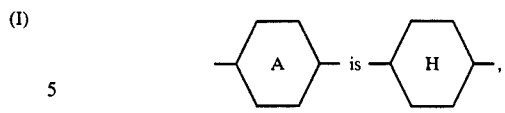

R¹ is preferably a straight-chain or branched alkyl group having 1 to 20 carbon atoms.

R² in general formula (I) above represents a straight-chain or branched alkyl group having 1 to 20 carbon atoms, but it preferably is a straight-chain alkyl group having 1 to 10 carbon atoms from the standpoint of easy availability of raw materials.

In general formula (I) above, the asymmetric carbon atoms at the 2- and 4-positions in the lactone ring each independently is of the (S) or (R) configuration. In the case of a chiral smectic liquid crystal, a cis configuration is preferred for use as a dopant, while in the case of a chiral nematic liquid crystal, the lactone ring may be of either a cis or trans configuration for use as a dopant.

The present invention also provides a liquid-crystal composition.

The liquid-crystal composition according to the present invention contains, as a constituent, at least one compound represented by general formula (I) given above. For use in ferroelectric liquid-crystal displays in particular, an Sc* liquid-crystal composition is selected in which at least one of the compounds of the above general formula (I) has been incorporated as part or all of the chiral dopant(s) in a base liquid crystal that is the main ingredient and exhibits an Sc phase.

Further, a composition obtained by incorporating a small quantity of at least one of the compounds of general formula (I) in a nematic liquid crystal can be used as a TN liquid crystal for the prevention of so-called reverse domain or as an STN liquid crystal, etc.

The present invention further provides an optically active compound represented by general formula (II), which is a novel, optically active lactone derivative used as a raw material for the production of the compound of general formula (I), and a process for producing the compound of general formula (II).

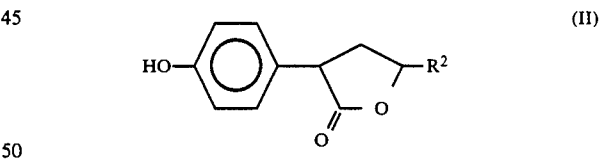
(II)

In the above formula, R² is the same as that in general formula (I) given hereinbefore.

The compound of general formula (II) can be synthesized as follows.

A phenylacetonitrile derivative represented by the following general formula (III) is reacted with an optically active epoxide represented by general formula (IV) by use of a strong base such as butyllithium or lithium diisopropylamide, thereby to obtain an optically active hydroxynitrile compound represented by general formula (V). The compound of general formula (V) also is a novel, optically active compound.

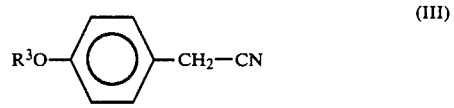
(III)

-continued

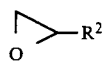

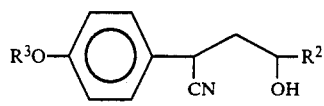

In general formulae (III) to (V) above, $R^3$ represents a lower alkyl group such as methyl or ethyl and $R^2$ is the same as that in general formula (I) above.

The compound of general formula (V) above is obtained in the form of a diastereomeric mixture.

Subsequently, the cyano group of the above-obtained compound of general formula (V) is hydrolyzed in an alkali to give a carboxylic acid, which is then cyclized by use of thionyl chloride etc. to obtain a lactone derivative represented by general formula (VI).

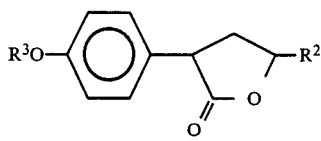

In the above formula, $R^3$ and $R^2$ are as defined in general formulae (III) and (I), respectively.

The above-obtained compound of general formula (VI) is a cis-trans mixture, but the isomers can be easily separated by a separating means such as column chromatography.

The compound of general formula (VI) is then subjected to dealkylation by use of ethanethiol etc. in the presence of a Lewis acid such as aluminum chloride, thereby to obtain a compound of general formula (II) above.

The compound of general formula (I) above can be obtained by reacting the above-obtained compound of general formula (II) with a compound of the following general formula (VII) in the presence of a basic substance such as pyridine.

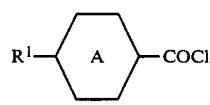

In the above formula, $R^1$ and

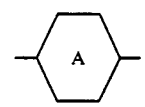

are the same as those in general formula (I). In practicing the above process, the combination of the absolute configuration at the 2-position and that at the 4-position in the lactone ring in each of the compounds of general formulae (I), (II), and (VI) can be any of (S)(S), (S)-(R), (R)-(S), and (R)-(R) by employing, as the compound of general formula (IV) above, those which are different in the absolute configuration at the 2position in their lactone rings.

The optically active lactone derivative of general formula (I) according to the present invention can be obtained as described above. Specific compounds that belong to such derivative of general formula(I) and specific intermediates that belong to the compounds of general formulae (II), (III), etc. can be identified by means of measurement of phase transition temperatures such as melting point, elementary analysis, infrared spectrophotometry (IR), nuclear magnetic resonance spectroscopy (NMR), and mass spectrometry (MS).

Examples of the compound represented by general formula(I) are listed in Table 1, in which "Cr" indicates a crystalline phase, "I" an isotropic liquid "N*" a chiral nematic phase, and "S*" a smectic phase that has not yet been identified with respect to smectic structure.

Further, ★ means that under rapid cooling conditions, the phase transition temperatures of the compound are unmeasurable because of crystallization, although the existence of the phases can be confirmed.

TABLE 1

Compounds of General Formula (I) with Their Phase Transition Temperatures (°C.)

| No. | Example | $R^1$ | A | Absolute Configuration at C*, C** | $R^2$ | Phase Transition Temperature |
|---|---|---|---|---|---|---|
| 1 | 5 | $C_8H_{17}O$ | phenyl | (R),(R) | $C_6H_{13}$ | 96.6 (Cr → I) <br> ★ (I → N*) |
| 2 | 6 | $C_8H_{17}O$ | phenyl | (S),(R) | $C_6H_{13}$ | 102.7 (Cr → I) <br> ★ (I → N*) |
| 3 | 7 | $C_8H_{17}$ | phenyl | (R),(R) | $C_6H_{13}$ | 94.9 (Cr → I) |

TABLE 1-continued

Compounds of General Formula (I) with Their Phase Transition Temperatures (°C.)

| No. | Example | R¹ | [A ring] | Absolute Configuration at C*, C** | R² | Phase Transition Temperature |
|---|---|---|---|---|---|---|
| 4 | 8 | (S)—C₂H₅CH(CH₃)—CH₂ | phenyl | (R),(R) | C₆H₁₃ | 84.0 (Cr →I) |
| 5 | 9 | C₈H₁₇ | phenyl | (S),(R) | C₆H₁₃ | 101.9 (Cr →I) |
| 6 | 10 | C₈H₁₇O | F-phenyl | (R),(R) | C₆H₁₃ | 103.5 (Cr →I) |
| 7 | 11 | C₇H₁₅ | H (cyclohexyl) | (R),(R) | C₆H₁₃ | 121.1 (Cr →I)<br>(I →S*) |

At room temperature, the compound of general formula (I) according to this invention does not stably exhibit liquid phases including an Sc* phase if used alone and, hence, is unsuited for use as a single liquid-crystal material, but suited for use in the form of a composition. Particularly in the case where such composition is for use as a ferroelectric liquid-crystal display device, it is effective to incorporate the compound of general formula (I), as part or all of the chiral dopant(s), into an Sc liquid-crystal composition having a low viscosity to give an Sc* liquid-crystal composition.

Examples of Sc compounds that are for use in Sc compositions to be doped with the compound of general formula (I), which is an optically active lactone derivative, include phenyl benzoate-type compounds such as those represented by the following general formula (A) and pyrimidine-type compounds represented by general formula (B):

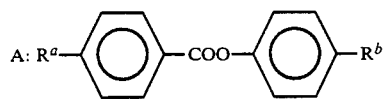

A: $R^a$—⟨phenyl⟩—COO—⟨phenyl⟩—$R^b$ wherein $R^a$ and $R^b$ are identical or different and independently represent a straight-chain or branched alkyl, alkoxyl, alkoxycarbonyl, alkanoyloxy, or alkoxycarbonyloxy group,

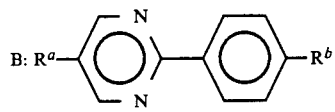

B: $R^a$—⟨pyrimidine⟩—⟨phenyl⟩—$R^b$ wherein $R^a$ and $R^b$ are the same as those in general formula A above.

Further, compounds represented by the following general formula (C), which includes general formulae (A) and (B), may be used for the same purpose:

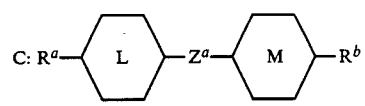

C: $R^a$—⟨L⟩—$Z^a$—⟨M⟩—$R^b$ wherein $R^a$ and $R^b$ are the same as those in general formula (A);

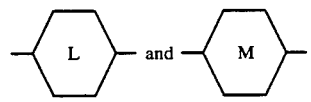

—⟨L⟩— and —⟨M⟩— are identical or different and independently represent

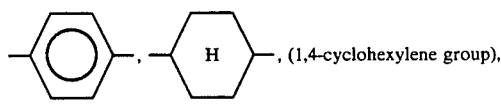

—⟨phenyl⟩—, —⟨H⟩—, (1,4-cyclohexylene group),

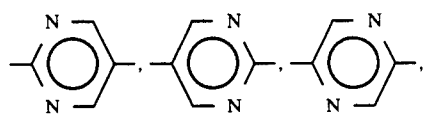

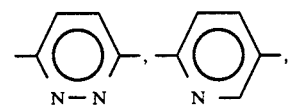

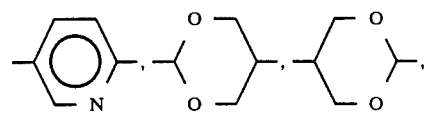

or halogen-substituted groups derived therefrom; and $Z^a$ represents —COO—, —OCO—, —CH$_2$O—, —OCH$_2$—, —CH$_2$CH$_2$—, —C≡C—, or a single bond.

For the purpose of widening the Sc-phase temperature range into a high-temperature region, a three-ring compound represented by general formula (D) may be used:

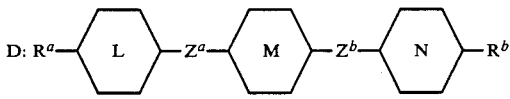

wherein $R^a$ and $R^b$ are the same as those in general formula (A);

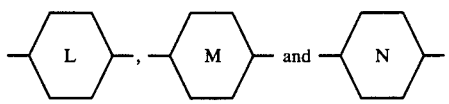

are identical or different and are the same as

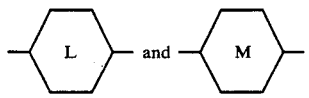

in general formula (C) above; and $Z^a$ and $Z^b$ are identical or different and are the same as $Z^a$ in general formula (C) above.

It is effective to use these compounds in the form of a Sc liquid-crystal composition obtained by mixing such compounds. Each compound is not necessarily required to exhibit an Sc phase as long as the resulting composition shows an Sc phase.

By incorporating as chiral dopant the compound of this invention represented by general formula (I) and, if needed, other optically active compound into the Sc liquid-crystal composition obtained above, a liquid-crystal composition that exhibits an Sc* phase over a wide temperature range including room temperature can be easily obtained.

The thus-obtained liquid-crystal composition is sandwiched between two transparent glass electrodes which have undergone orientation treatment, in such a manner that the composition is enclosed in the form of a thin film about 1 to 20 μm thick. This construction is used as a liquid-crystal display cell.

In order to obtain good contrast, the cell should be of a monodomain structure in which orientation is uniform. For this purpose, many attempts have so far been made. It is generally known that a liquid-crystal material showing food orientation characteristics is one which, upon cooling, undergoes phase transition changing from an isotropic liquid (I) phase through a chiral nematic (N*) phase to either an Sc* phase or an $S_A$ phase and then an Sc* phase, and which has a long helical pitch in the N* and Sc* phases, particularly in the N* phase.

For increasing the helical pitch, chiral compounds different from each other in twist direction are mixed in suitably proportions to give a composition for use as a chiral dopant. In this case, however, care must be taken not to cause spontaneous polarizations to negate each other.

The direction of spontaneous polarization induced by the compound of this invention represented by general formula (I), in which at least two asymmetric carbon atoms are present (at the 2- and 4-positions in the lactone ring), and the direction of helical pitch are respectively ⊕ and left in the case where both absolute configurations at the 2- and 4-positions in the lactone ring are (R), and ⊖ and right in the case where both absolute configurations are (s). (The direction of spontaneous polarization is determined based on the definition that the spontaneous polarization of (S)-2-methylbutyl p-decyloxybenzylidene-aminocinnamate (DOBAMBC), well known as a ferroelectric liquid crystal, is in the direction of ⊖.

Therefore, by combining with an optically active known compound in which the direction of spontaneous polarization induced and the direction of helical pitch are either ⊕ and right or ⊖ and left, the helical pitch can be elongated without causing the spontaneous polarizations to negate each other.

Examples of such a compound include compounds having as an optically active group,

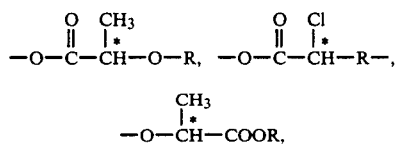

and the like.

In the case of a compound having an optically active group which induces very weak spontaneous polarization, such as

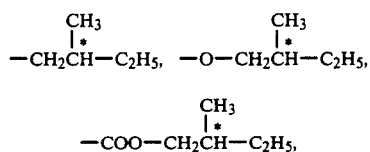

or the like and having no other optically active groups, it is possible to blend such a compound with the compound of general formula (I) while only the direction of helical pitch is being considered, because the spontaneous polarization due to such a group is far smaller than that of the compound of general formula (I).

The compound of general formula (I) according to the present invention includes compounds which contain an asymmetric carbon atom in $R^1$ other than those at the 2- and 4-positions in the lactone ring.

The presence of an asymmetric carbon atom in $R^1$ serves, according to its absolute configuration, to further enhance the spontaneous polarization or to elongate or shorten the helical pitch.

For example, in the case where Compound No. 1 (Table 1) is incorporated in an amount of 5% in base liquid crystals (A) (vide infra) which exhibits an Sc phase, the helical pitch induced in the N* phase is as short as 2.4 μm while in the case of Compound No. 4 (Table 1) in which (S)-2-methylbutyl group that induces helical in the opposite direction has been incorporated as R, the pitch is as long as 5.0 μm, so that pitch adjustment has become easier.

The most characteristic feature of the compound of general formula (I) resides in that incorporation of the compound as a chiral dopant even in a small quantity enables the resulting composition to show very strong spontaneous polarization.

As will be demonstrated in an Example given later, an Sc* composite obtained by incorporating the compound of general formula (I) according to this invention into base liquid crystal (A) in an amount of 5% shows a spontaneous polarization of about 15 nC/cm², and 10% incorporation results in a spontaneous polarization as high as 35 nC/cm². These values are found to be considerably large in view of the fact that DOBAMBC described above shows spontaneous polarization of 2 to 3 nC/cm² even when used alone.

The base liquid crystal (A) used above has the following composition. Compounds of general formula (B):

Compounds of general formula (B):

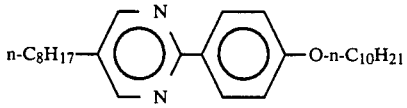  21.4 wt %

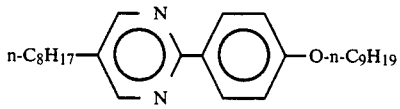  18.2 wt %

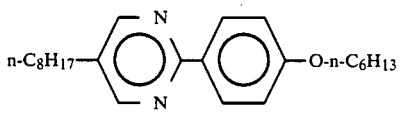  9.6 wt %

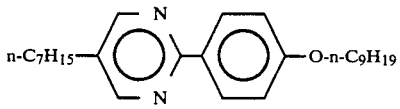  12.3 wt %

Compounds of general formula (C):

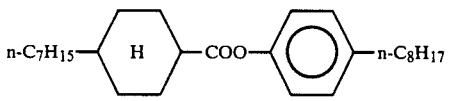  8.1 wt %

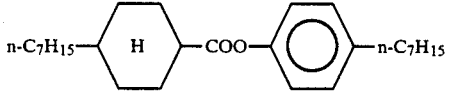  8.1 wt %

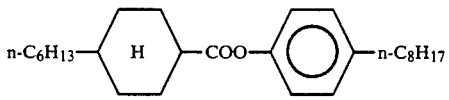  4.1 wt %

Compounds of general formula (D):

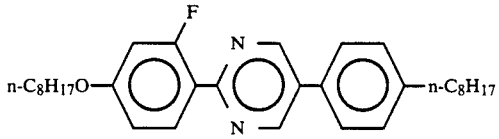  7.3 wt %

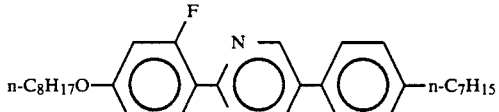  7.3 wt %

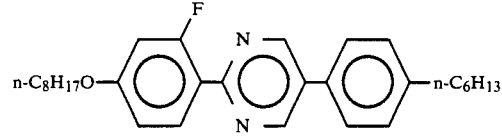  3.6 wt %

Such base liquid crystal (A) exhibited an N phase at temperature not higher than 76.5° C., an $S_A$ phase at temperatures not higher than 65° C., and an Sc phase at temperatures not higher than 43° C., and had a melting point of −3° C.

One of the excellent features of the compound of general formula (I) is that when incorporated in a base liquid crystal, the compound never lowers the upper limit of the Sc* phase temperatures of the resulting liquid crystal, although the compound per se does not exhibit an Sc* phase.

The upper limit of the Sc phase temperatures of the above-described base liquid crystal (A) is 43° C., whereas the upper limit of the Sc* phase temperatures of an Sc* composition obtained by incorporating Compound No. 1 of Table 1 in base liquid crystal (A) in an amount of 5% is 52.5° C., which is higher than the above value by as large as 9.5° C. Because of such nature, the compound of general formula (I) is useful as a chiral dopant.

Furthermore, by the incorporation of only a small quantity of the compound of general formula (I) in ordinary nematic liquid crystals, short helical pitches can be induced, such helical pitches changing very little with temperature. Therefore, the compound of general formula (I) can be used with ordinary TN liquid crystals for the prevention of so-called reverse domain, and also be effectively used in blends with STN liquid crystals.

The present invention will be explained below in more detail by reference to the following Examples, which should not, of course, be construed to be limiting the spirit and scope of the invention.

In the Examples, the structures of compounds were determined by nuclear magnetic resonance spectroscopy (NMR), infrared spectrophotometry (IR), and mass spectrometry (MS). Phase transition temperatures were measured by means of a polarizing microscope equipped with a temperature-regulating stage and a differential scanning calorimeter (DSc). In the IR data, (KBr) indicates on formed tablets, while (neat) indicates on liquid films. In the NMR data, (CDCl₃) and (CCl₄) indicate solvents, while "s" means a singlet, "d" a doublet, and "t" a triplet. Further, "dd" means a double doublet, this applying correspondingly to "td", "ddt", "ddd", "dt", "tt", etc., while "broad" means a broad absorption. "J" indicates the coupling constant. In the MS data, "M*" indicates a parent peak and the values in parentheses show the relative intensities for respective peaks. "R$_f$" shows R$_f$values obtained in thinlayer chromatography. Temperature values are given in terms of ° C. All percents indicating compositions are by weight.

The absolute configurations for each compound were determined by the comparison of NMR spectra with a compound having a similar partial structure and described in JCS Perkin I 1480 (1975).

EXAMPLE 1

Synthesis of (2R,4R)- and (2S, 4R)-4-hydroxy-2-(4methoxyphenyl)decanenitriles

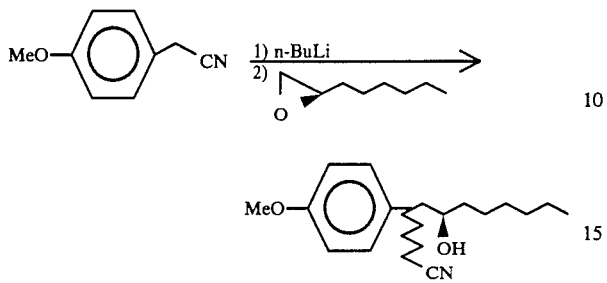

To a solution of 750 mg of 4-methoxyphenylacetonitrile in 10 ml of tetrahydrofuran (THF) was added 3.3 ml of a 1.55 M hexane solution of butyllithium (n-BuLi) at −78° C. This mixture was stirred for 1 hour, and then a solution of 651 mg of (2R)-1, 2-epoxyoctane in 5 ml of THF was added. The temperature of the resulting mixture was raised to −10° C. A saturated aqueous solution of ammonium chloride was then added, and the resulting mixture was subjected to extraction with ether, followed by column chromatography (Kieselgel 60, hexane/ethyl acetate =4/1), thereby obtaining 926 mg (yield 70%) of an about 1:1 mixture of (2R,4R)- and (2S,4R)-4-hydroxy -2-(4-methoxyphenyl)decanenitriles. This mixture was subjected directly to the subsequent treatment. The two products can be separated by means of medium-pressure column chromatography.

Identification of (2R,4R)-4-hydroxy-2-(4-methoxyphenyl)-decanenitrile

Oily substance, $R_f$ 0.24 (hexane/ethyl acetate=3/1) $[\alpha]_D^{20}$ −20.8° (c=2.06, MeOH).

IR (neat) 3450, 2240, 1610, 1510, 1250, 1030, 825, 625 cm$^{-1}$.

$^1$H NMR (CDCl$_3$) δ0.86 (t, J=6.8Hz, 3H), 1.18~1.48 (m, 10H), 1.50 (broad s, 1H), 1.96 (ddd, J=13.8, 9.9, 3.2Hz, 1H), 2.08 (ddd, J=13.8, 9.7, 5.3Hz, 1H), 3.39 (m, 1H), 3.81 (s, 3H), 4.01 (dd, J=9.9, 5.3Hz, 1H), 6.90 (d, J=8.7Hz, 2H), 7.26 (d, J=8.7, 2H).

MS m/z: 275 (M+, 4.0), 159 (100).

Elementary analysis: Calculated for C$_{17}$H$_{25}$NO$_2$ : C, 74.14; H, 9.15; N, 5.09%. Found : C, 73.80; H, 9.24; N, 4.92%.

Identification of (2R,4R)-4-hydroxy-2-(4-methoxyphenyl)-decanenitrile

Oily substance, $R_f$ 0.29 (hexane/ethyl acetate=3/1) $[\alpha]_D^{20}$ −29.5° (c=2.61, MeOH).

IR (neat) 3450, 2240, 1610, 1510, 1250, 1175, 1030, 825, 625 cm$^{-1}$.

$^1$H NMR (CDCl$_3$) δ0.88 (t, J=7.0Hz, 3H), 1.22~1.54 (m, 10H), 1.65 (broad s, 1H), 1.80 (ddd, J=13.9, 10.5, 4.4Hz, 1H), 1.98 (ddd, J=13.9, 11.5, 2.4Hz 1H), 3.39 (m, 1H), 3.81 (s, 3H), 4.01 (dd, J=11.5, 4.4Hz, 1H), 6.90 (d, J=8.7Hz, 2H), 7.27 (d, J=8.7, 2H).

MS m/z: 275 (M+, 3.0), 159 (100).

Elementary analysis: Calculated for C$_{17}$H$_{25}$NO$_2$ : C, 74.14; H, 9.15; N, 5.09%. Found : C, 73.84; H, 9.02; N, 4.81%.

EXAMPLE 2

Synthesis of (2R,4R)- and (2S,4R)-2-(4-methoxyphenyl)-4-decanolides

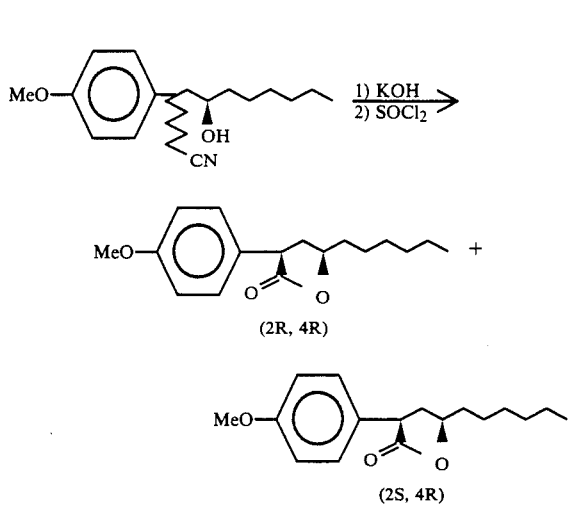

To a solution of 792 mg of an about 1:1 mixture of (2R,4R)- and (2S,4R)-4-hydroxy-2-(4-methoxyphenyl) decanenitriles in 28 ml of diethylene glycol was added 35 ml of 40% aqueous potassium hydroxide solution. This mixture was stirred at 100° C for 5 hours. Concentrated sulfuric acid was added to adjust the pH of the reaction mixture to 1, and the reaction product was then extracted with ethyl acetate. The organic layer was washed with saturated sodium chloride aq. solution and then concentrated. To the resulting residue were added 15 ml of dichloromethane and 0.25 ml of thionyl chloride. This mixture was stirred at room temperature for 30 minutes. Saturated sodium chloride aq. solution was added thereto. The resulting mixture was subjected to extraction with dichloromethane, followed by separation and purification by column chromatography (Kieselgel 60, hexane/ethyl acetate =15/1). Thus, 420 mg (yield 52%) of (2R,4R)-2-(4-methoxyphenyl)-4-decanolide and 351 mg (yield 44%) of (2S,4R)-2-(4-methoxyphenyl)-4-decanolide were obtained.

Identification of (2R,4R)-2(4-methoxyphenyl)-4-decanolide

Melting point 68° C., $R_f$ 0.42 (hexane/ethyl acetate=3/1) $[\alpha]_D^{20}$ +2.8° (c=1.42, MeOH).

IR (KBr) 2940, 1740, 1515, 1250, 1190, 1030 cm$^{-1}$ $^1$H NMR (CDCl$_3$) δ0.90 (t, J=6.8Hz, 3H), 1.26~1.56 (m, 8H), 1.63~1.72 (m, 1H), 1.79~1.88 (m, 1H), 2.00 (td, J=12.6, 10.5Hz, 1H), 2.72 (ddd, J=12.6, 8.6, 5.4Hz, 1H), 3.80 (s, 3H), 3.84 (dd, J=12.6, 8.6Hz, 1H), 4.46 (ddt, J=10.5, 7.3, 5.4Hz, 1H), 6.90 (d, J=8.9Hz, 2H), 7.19 (d, J=8.5Hz, 2H).

MS m/z: 276 (M+,14.3), 147 (100), 134 (34.6).

Elementary analysis: Calculated for C$_{17}$H$_{24}$NO$_3$ : C, 73.88; H, 8.75%. Found : C, 74.07; H, 8.77%.

Identification of (2R,4R)-2(4-methoxyphenyl)-4-decanolide

Melting point 32.5-33.5° C., $R_f$ 0.50 (hexane/ethyl acetate=3/1). $[\alpha]_D^{20}$ +53.8° (c=1.06, MeOH).

IR (KBr) 2930, 1760, 1515, 1250, 1175, 1030 cm$^{-1}$.

$^1$H NMR (CDCl$_3$) δ0.89 (t, J=6.7Hz, 3H), 1.26~1.56 (m, 8H), 1.68~1.59 (m, 1H), 1.84~1.75 (m, 1H), 2.35 (ddd, J=13.1, 9.3, 5.8Hz, 1H), 2.47 (dt, J=13.1, 7.1Hz, 1H), 3.79 (s, 3H), 3.85 (dd, J=9.3, 7.1Hz, 1H), 4.61 (tt, J=7.4, 5.7Hz, 1H), 6.91 (d, J=8.8Hz, 2H), 7.18 (d, J=6.6Hz, 2H).

MS m/z: 276 (M+,13.3), 147 (100), 134 (35.3) 121 (22.4).

Elementary analysis: Calculated for $C_{17}H_{24}NO_3$ : C, 73.88; H, 8.75%. Found : C, 73.63; H, 8.75%.

EXAMPLE 3

Synthesis of (2R,4R)-2-(4-hydroxyphenyl)-4-decanolide

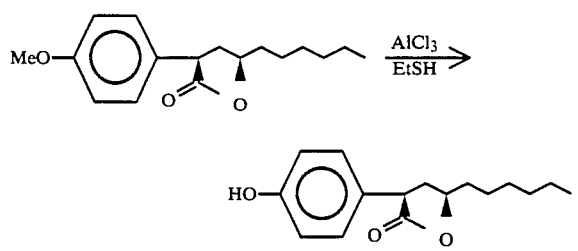

To a solution of 1.6 g of aluminium chloride and 2 ml of ethanethiol in 15 ml of dichloromethane was added, at 0° C, a solution of 440 mg of (2R,4R)-2-(4-methoxyphenyl)-4-decanolide dissolved in 5 ml of dichloromethane. This mixture was stirred for 4 hours. A saturated sodium bicarbonate aq. solution was then added, and the resulting mixture was subjected to extraction with dichloromethane, followed by column chromatography (Kieselgel 60, hexane/ethyl acetate = 3/1), thereby obtaining 374 mg (yield 90%) of (2R,4R)-2-(4-hydroxyphenyl)-4-decanolide. Identification data for this product are as follows. Melting point 87–88° C. $[\alpha]_D^{20}$ +3.2° (c=1.27, MeOH).

IR (KBr) 3480, 2940, 2875, 1740, 1520, 1440, 1355, 1260, 1185, 990, 815 cm$^{-1}$.

$^1$H NMR (CDCl$_3$) δ0.90 (t, J=6.9Hz, 3H), 1.26~1.56 (m, 8H), 1.64~1.72 (m, 1H), 1.79~1.89 (m, 1H), 1.99 (td, J=12.7, 10.5Hz, 1H), 2.72 (ddd, J=12.7, 8.7, 5.3Hz, 1H), 3.81 (dd, J=12.7, 8.7Hz, 1H), 4.47, (ddt, J=12.5, 7.3, 5.4Hz, 1H), 5.3 (broad s, 1H), 6.77 (d, J=8.6Hz, 2H), 7.07 (d, J=8.5Hz, 2H).

MS m/z: 262 (M+,7.7), 133 (100), 120 (57.8) 107 (22.6).

Elementary analysis: Calculated for $C_{16}H_{22}NO_3$ : C, 73.25; H, 8.45%. Found : C, 73.22; H, 8.52%.

EXAMPLE 4

Synthesis of (2S,4R)-2-(4-hydroxyphenyl)-4-decanolide

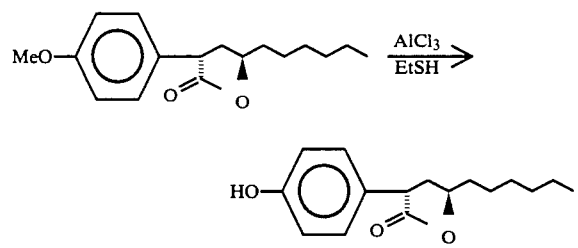

In the same manner as in Example 3 (synthesis of (2R,4R)-2-(4-hydroxyphenyl)-4-decanolide) 298 mg (yield 92% of (2S,4R)-2-(4-hydroxyphenyl)-4-decanolide was obtained from 340 mg of (2R,4R)-2-(4-methoxyphenyl)-4-decanolide. Identification data for this product are as follows. Melting point 35–36° C. $[\alpha]_D^{20}$ +47.8° (c=1.54, MeOH).

IR (KBr) 3480, 2940, 1738, 1520, 1220, 1195, 830 cm$^{-1}$.

$^1$H NMR (CDCl$_3$) δ0.89 (t, J=6.8Hz, 3H), 1.26~1.54 (m, 8H), 1.59~1.68 (m, 1H), 1.75~1.83 (m, 1H), 2.35 (ddd, J=13.1, 9.4, 5.4Hz, 1H), 2.46 (dt, J=13.1, 7.1Hz, 1H), 3.83 (dd, J=9.4, 7.1Hz, 1H) 4.63 (tt, J=7.5, 5.6Hz, 1H), 5.4 (broad s, 1H), 6.78 (d, J=8.6Hz, 2H), 7.08 (d, J=8.5Hz 2H).

MS m/z: 262 (M+,4.7), 133 (100.0), 120 (61.7).

Elementary analysis: Calculated for $C_{16}H_{22}NO_3$ : C, 73.25; H, 8.45%. Found : C, 73.33; H, 8.50%.

EXAMPLE 5

Synthesis of (2R, 4 R)-2-{(4-octyloxybenzoyloxy)phenyl}- 4-decanolide (Compound No. 1 in Table 1)

In 4 ml of dichloromethane were dissolved 50 mg of (2R,4R)-2-(4-hydroxyphenyl)-4-decanolide obtained in Example 3 and 49 mg of 4-octyloxybenzoyl chloride. To this solution was added 1 ml of pyridine. The resulting mixture was stirred for 6 hours under heating to reflux. The reaction mixture was allowed to cool, and then 50 ml of ether and diluted hydrochloric acid were added thereto. The resulting organic layer was separated, washed with water, and then dried with anhydrous sodium sulfate. The solvent was removed by evaporation and the resulting crude produce was purified by silica gel column chromatography, thereby obtaining 65 mg of crystals of the desired compound (yield 70%).

The compound obtained above was recrystallized from ethanol and the phase transition temperatures thereof were measured. As a result, its melting point was found to be 96.6° C. Under rapid cooling conditions, the presence of an N* phase was confirmed, but the transition temperatures could not be measured because the compound crystallized. Identification data for the compound are as follows.

IR: 1765, 1730, 1610, 1520, 1320, 1260, 1210, 1170, 1130, 1080, 970, 935, 880, 850, 765 cm$^{-1}$.

NMR: δ=8.12 (d, 2H), 7.33 (d, 2H), 7.20 (d, 2H), 6.96 (d, 2H), 4.49 (m, 1H), 4.03 (t, 2H), 3.90 (dd, 1H), 2.76 (m, 1H), 2.03 (td, 1H), 1.80 (m, 3H), 1.69 (m, 1H), 1.2~1.6 (m, 18H), 0.90 (broad t, 6H).

EXAMPLES 6 to 11

The same procedures as in Example 5 were repeated except that (2S, 4R)-2-(4-hydroxyphenyl)-4-decanolide was used in place of (2R, 4R)-2-(4-hydroxyphenyl)-4-decanolide, thereby obtaining (2S, 4R)-2-{4-(4-octyloxybenzoyloxy)phenyl}-4-decanolide (Compound No. 2 in Table 1). (Example 6)

The same procedures as in Example 5 were repeated except that 4-octylbenzoyl chloride was used in place of 4-octyloxybenzoyl chloride, thereby obtaining (2S, 4R)-2-{4-(4-octyloxybenzoyloxy)phenyl}-4-decanolide (Compound No. 3 in Table 1). (Example 7)

Likewise, Compounds No. 4 to No. 7 as shown in Table 1 were obtained. (Examples 8 to 11 )

EXAMPLE 12

(Preparation of Sc* liquid-crystal composition and display device)

An Sc* liquid-crystal composition was prepared by incorporating Compound No. 1 of Table 1 into base liquid crystal (A) described hereinbefore in an amount of 5%. Phase transition temperatures of this composition are as follows.

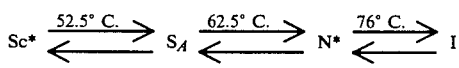

The above-obtained Sc* liquid-crystal composition was heated to give an isotropic liquid, which was packed in an about 2 μm thick cell whose one side had been alligned by polymide-rubbing treatment. The resulting cell was cooled slowly to thereby give an oriented Sc* phase. Square waves having an electric field intensity of 10 $V_{p-p}/\mu m$ were applied to the thus-obtained display element to measure its electro-optic response time. As a result, the display element was ascertained to show good high-speed response, i.e., 51 microseconds at 25° C. In this electric field, the liquid-crystal composition in the cell showed spontaneous polarizations of 14.5 n/C/cm² (25° C.) and 13.3 nC/cm² (30° C.) and tilt angles of 24.6° (25° C.) and 23.2° (30° C.).

Subsequently, the amount of Compound No. 1 incorporated was changed to 10% to prepare an Sc* liquid-crystal composition. Phase transition temperatures of this composition are as follows.

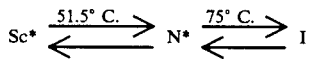

The response time likewise measured at 25° C. was 76 microseconds and the spontaneous polarization and tilt angle, measured at the same time, were 35.4 nC/cm² and 28.3°, respectively.

Thereafter, Compound No. 2 in Table 1 was used in place of Compound No. 1 in Table 1 in an amount of 5% to prepare and Sc* liquid-crystal composition. Phase transition temperatures of this composition are as follows.

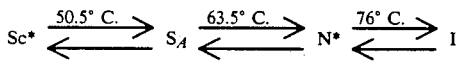

The response time likewise measured at 30° C. was 470 microseconds and the spontaneous polarization and tilt angle, measured at the same time, were as small as 0.1 nC/cm² or less and 16.9°, respectively.

EXAMPLE 13

An Sc* liquid-crystal composition was prepared which was composed of 90% of base liquid crystal (A) described hereinbefore, 5% of Compound No. 4 in Table 1, and 5% of the compound of the formula

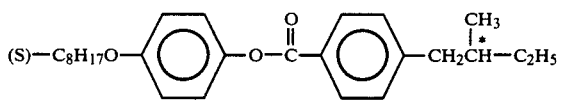

This composition exhibited an Sc* phase at temperatures not higher than 44.8° C.

This composition exhibited an N* phase over a temperature range of from 70.4° C. to 45° C., where the helical pitch was as long as 15 μm or more.

EXAMPLE 14

A chiral nematic liquid-crystal composition was prepared which was composed of 97% of a base liquid crystal exhibiting a nematic phase at around room temperature and 3% of Compound No. 1 in Table 1.

The helical pitch of this composition was as follows.

| 70° C. | 5.8 μm |
|--------|--------|
| 25° C. | 5.9 μm |

The above results show that the helical pitch of the composition is short and its temperature dependence is very little.

The formulation for the base liquid crystal used above was as follows.

[Structures: C₃H₇-cyclohexyl-COO-phenyl-OC₂H₅ (33%); C₄H₉-cyclohexyl-COO-phenyl-OC₂H₅ (33%); C₅H₁₁-cyclohexyl-COO-phenyl-OCH₃ (34%)]

When the compound of general formula (I) according to the present invention is mixed as a chiral dopant with a base liquid-crystal compound or composition to give an Sc* liquid-crystal composition, very strong spontaneous polarization can be induced even where the amount of the compound incorporated is small.

The compound of this invention can also be used with TN liquid crystals, STN liquid crystals, etc., because the helical pitch induced in the N* phase is sufficiently short and its temperature dependence is little even where the compound is incorporated in a small quantity. It is also possible to obtain a compound that shows a long pitch by suitably selecting side chains.

Furthermore, the industrial production of the compound of this invention is easy as demonstrated in Examples, and the compound per se is colorless and chemically stable to light, water, heat, etc. and, hence, is of good practical use.

Moreover, the ferroelectic liquid-crystal compound according to this invention and compositions containing the compound of this invention have good orientation characteristics and show exceedingly high response speeds that are not less than 100 times that of conventional nematic liquid crystals, and hence they are extremely useful as liquid-crystal device materials.

While the invention has been described in detail and with reference to specific embodiments thereof, it will be apparent to one skilled in the art that various changes and modifications can be made therein without departing from the spirit and scope thereof.

What is claimed is:

1. An optically active lactone derivative represented by the following general formula (I):

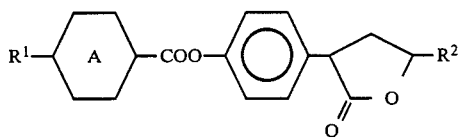

(I)

wherein $R^1$ represents a straight-chain or branched alkyl, or alkoxyl, group having 1 to 20 carbon atoms with or without an optically active carbon, $R^2$ represents a straight-chain alkyl group having 1 to 20 carbon atoms,

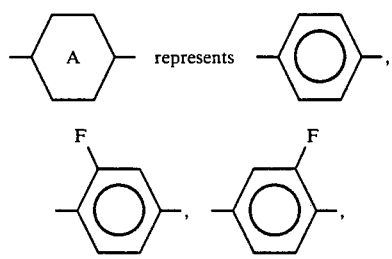

or trans-1, 4-cyclohexylene group of the formula

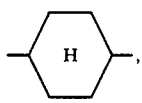

and the assymmetric carbon atoms at the 2- and 4-positions in the lactone ring each independently is of the (S) or (R) configuration.

2. An optically active lactone derivative as claimed in claim 1, wherein $R^1$ is a straight-chain or branched alkyl or alkoxyl group having 1 to 20 carbon atoms.

3. An optically active lactone derivative as claimed in claim 2, wherein the lactone ring is of a cis-substituted configuration.

4. An optically active lactone derivative as claimed in claim 3, wherein both of the absolute configuration at the 2-position and that at the 4-position in the lactone ring are (R).

5. An optically active lactone derivative as claimed in claim 2, wherein the absolute configuration at the 2-position and that at the 4-position in the lactone ring are (S), and (R).

6. An optically active lactone derivative as claimed in claim 4, wherein

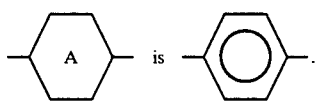

7. An optically active lactone derivative as claimed in claim 5, wherein

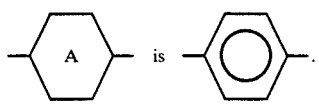

8. An optically active lactone derivative as claimed in claim 6, wherein $R^1$ is a straight-chain or branched alkyl or alkoxyl group having 1 to 20 carbon atoms.

9. An optically active lactone derivative as claimed in claim 7, wherein $R^1$ is a straight-chain or branched alkyl or alkoxyl group having 1 to 20 carbon atoms.

10. An optically active lactone derivative as claimed in claim 6, wherein $R^1$ is an optically active, branched alkyl or alkoxyl group having 1 to 20 carbon atoms.

11. An optically active lactone derivative as claimed in claim 8, wherein $R^1$ is $C_8H_{17}O$ and $R^2$ is $C_6H_{13}$.

12. An optically active lactone derivative as claimed in claim 8, wherein $R^1$ is $C_8H_{17}$ and $R^2$ is $C_6H_{13}$.

13. An optically active lactone derivative as claimed in claim 9, wherein $R^1$ is $C_8H_{17}O$ and $R^2$ is $C_6H_{13}$.

14. An optically active lactone derivative as claimed in claim 9, wherein $R^1$ is $C_8H_{17}$ and $R^2$ is $C_6H_{13}$.

15. An optically active lactone derivative as claimed in claim 10, wherein $R^1$ is $$(S)-C_2H_5\overset{\overset{\displaystyle CH_3}{|}}{C}H-CH_2-$$

and $R^2$ is $C_6H_{13}$.

16. An optically active lactone derivative as claimed in claim 4, wherein

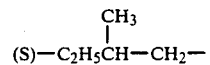

17. An optically active lactone derivative as claimed in claim 16, wherein $R^1$ is a straight-chain or branched alkyl or alkoxyl group having 1 to 20 carbon atoms.

18. An optically active lactone derivative as claimed in claim 17, wherein $R^1$ is $C_8H_{17}O$ and $R^2$ is $C_6H_{13}$.

19. An optically active lactone derivative as claimed in claim 4, wherein

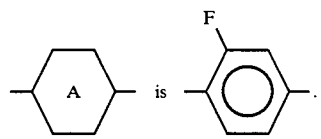

20. An optically active lactone derivative as claimed in claim 19, wherein $R^1$ is a straight-chain or branched alkyl or alkoxyl group having 1 to 20 carbon atoms.

21. An optically active lactone derivative as claimed is claim 20, wherein $R^1$ is $C_7H_{15}$ and $R^2$ is $C_6H_{13}$.

22. A liquid-crystal composition containing the optically active lactone derivative as claimed in claim 1.

23. A liquid-crystal composition as claimed in claim 22, which exhibits a chiral nematic phase.

24. A liquid-crystal composition as claimed in claim 22, which exhibits a chiral smectic phase.

25. A liquid-crystal composition comprising an optically inactive liquid-crystal compound or composition exhibiting a smectic C phase and, incorporated therein, a chiral dopant comprising an optically active compound, said chiral dopant containing at least one of the optically active lactone derivatives as claimed in claim 1.

26. A liquid-crystal display device employing the liquid-crystal composition as claimed in claim 23.

27. A ferroelectric liquid-crystal display device employing the liquid-crystal composition as claimed in claim 24.

28. A ferroelectric liquid-crystal display device employing the liquid-crystal composition as claimed in claim 25.

* * * * *